United States Patent
Hasse et al.

(10) Patent No.: US 6,840,927 B2
(45) Date of Patent: Jan. 11, 2005

(54) TAMPON WITH FLUID WICKING OVERWRAP WITH SKIRT PORTION

(75) Inventors: Margaret Henderson Hasse, Wyoming, OH (US); Steven Ray Gilbert, Fairfield, OH (US); Eric Patton Weinberger, Fairfield, OH (US); Sharon Darlene Kirkpatrick, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 138 days.

(21) Appl. No.: 09/993,988

(22) Filed: Nov. 16, 2001

(65) Prior Publication Data

US 2003/0097108 A1 May 22, 2003

(51) Int. Cl.⁷ .............................................. A61F 13/20
(52) U.S. Cl. ........................... 604/385.18; 604/385.17; 604/904
(58) Field of Search ...................... 604/385.17, 385.18, 604/904, 363

(56) References Cited

U.S. PATENT DOCUMENTS

| | | | |
|---|---|---|---|
| 3,732,866 A | | 5/1973 | Accavallo |
| 3,854,481 A | * | 12/1974 | Messing |
| 4,027,673 A | | 6/1977 | Poncy et al. |
| 4,816,100 A | * | 3/1989 | Friese |
| 5,084,038 A | * | 1/1992 | Sheldon et al. |
| 5,185,010 A | * | 2/1993 | Brown, Jr. |
| 5,827,256 A | * | 10/1998 | Balzar |
| 5,891,123 A | | 4/1999 | Balzar |
| 6,186,995 B1 | | 2/2001 | Tharpe, Jr. |
| 6,258,075 B1 | * | 7/2001 | Taylor et al. .......... 604/385.18 |
| 6,554,814 B1 | * | 4/2003 | Agyapong et al. |
| 2002/0026177 A1 | * | 2/2002 | Lochte et al. |

FOREIGN PATENT DOCUMENTS

| | | |
|---|---|---|
| GB | 2 227 666 A | 8/1990 |
| JP | 08-117282 | 5/1996 |

* cited by examiner

Primary Examiner—Larry I. Schwartz
Assistant Examiner—Michele Kidwell
(74) Attorney, Agent, or Firm—Bridget D. Murray; Kevin C. Johnson

(57) ABSTRACT

An improved absorbent catamenial tampon having increased leakage protection and ability to readily absorb fluid while not aggressively adhering to tissue. This is accomplished with a tampon comprising a compressed absorbent member comprising an absorbent material. The compressed absorbent member of the tampon has an inner region and an exterior surface. The fluid wicking overwrap substantially covers the exterior surface of the compressed absorbent member, substantially permeates the inner region of the compressed absorbent member and extends beyond the withdrawal end to form a skirt portion. A method of making a tampon of the present invention is also disclosed.

11 Claims, 2 Drawing Sheets

TAMPON WITH FLUID WICKING OVERWRAP WITH SKIRT PORTION

FIELD OF THE INVENTION

This invention relates to an improved absorbent catamenial tampon having increased leakage protection and ability to readily absorb fluid. This is accomplished with a tampon made from a compressed absorbent member comprising an absorbent material. A fluid wicking overwrap substantially covers the exterior surface of the compressed absorbent member, substantially permeates the inner region of the compressed absorbent member and extends beyond the withdrawal end to form a skirt portion.

BACKGROUND OF THE INVENTION

A wide variety of absorbent catamenial tampons have long been known in the art. While it has been found that these tampons perform their intended function tolerably well, even the best of them do not always re-expand sufficiently, or fast enough, to provide good coverage against leakage. Another common problem with tampons is "bypass" failure that occurs when the menses travels along the length of the vagina without contacting the tampon, i.e., the tampon fails to intercept the flowing menses. During a tampon change, some residual menses may be left near the introitus of the vagina. This may be fluid which was previously absorbed, but which subsequently "squeezed out" of the tampon as it was withdrawn through the sphincter of the vagina. Such residual fluid, particularly if located near the introitus (i.e., in the lower vaginal cavity) may not be effectively absorbed by the replacement tampon. It has been desirable to find a mechanism to absorb bypassed fluid from the lower vaginal cavity. As well, there is a need for materials or treatments for use on the exterior surface of tampons that have a strong affinity for fluid.

The superior design of the present invention will achieve all these goals, as will be seen from the following discussions.

BACKGROUND ART

U.S. Pat. No. 6,186,995 issued to John M. Tharpe on Feb. 13, 2001 relates to VAGINAL TAMPON AND METHOD FOR FABRICATION THEREOF.

SUMMARY OF THE INVENTION

This invention relates to catamenial tampons having a compressed absorbent member comprising an absorbent material. The compressed absorbent member of the tampon has an inner region and an exterior surface. The absorbent material has a first surface opposed to a second surface and an insertion end opposed to a withdrawal end. The fluid wicking overwrap substantially covers the first surface and the second surface of the absorbent material. The fluid wicking overwrap extends beyond the withdrawal end of the absorbent material to form a skirt portion. The fluid wicking overwrap substantially covers the exterior surface of the compressed absorbent member and a portion of the fluid wicking overwrap substantially permeates the inner region of the compressed absorbent member.

The present invention also relates to a process for making a tampon comprising the step of providing an absorbent material having a first surface opposed to a second surface and an insertion end opposed to a withdrawal end. Next, a fluid wicking overwrap is provided. A wrapped absorbent is created by substantially covering said first surface and second surface with said fluid wicking overwrap. The fluid wicking overwrap extends beyond the withdrawal end of the absorbent material to form a skirt portion. The wrapped absorbent is then rolled or folded and/or compressed to form a compressed absorbent member with a skirt, said absorbent member having a vaginally insertable shape. The compressed absorbent member has an inner region and an exterior surface. Upon compression the fluid wicking overwrap substantially covers the exterior surface and substantially permeates the inner region of the compressed absorbent member.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

DETAILED DESCRIPTION OF THE INVENTION

Figure 1:
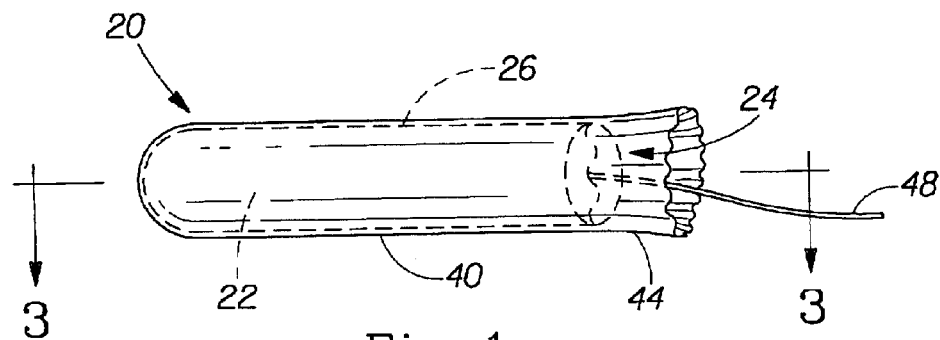
FIG. 1 is a perspective view of a tampon of the present invention incorporating a compressed absorbent member and fluid wicking overwrap covering the exterior surface and forming a skirt.

The present invention utilizes a fluid wicking overwrap that covers the exterior surface of the compressed absorbent member, substantially permeates the inner region of the compressed absorbent member and extends beyond the withdrawal end to form a skirt. This fluid wicking overwrap may comprise a fibrous non-woven material comprising a blend of synthetic and natural fibers that readily absorbs or wicks fluid. The skirt constructed from the fluid wicking overwrap draws bypassed fluid from the bottom of the vagina, thereby increasing absorbency and minimizing bypass discharge. The portion of the fluid wicking overwrap that substantially permeates the inner region of the compressed absorbent member allows for more complete utilization of the absorbent material and quick expansion providing good coverage against leakage.

As used herein the term "tampon" refers to any type of absorbent structure that is inserted into the vaginal canal for the absorption of fluid therefrom. Typically, tampons are constructed from an absorbent material that has been compressed into a vaginally insertable shape.

As used herein the terms "pledget" or "tampon pledget" are intended to be interchangeable and refer to a construction of absorbent material prior to the compression of such construction into a tampon.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

As used herein "fluid wicking" refers to the ability of a material to carry fluid or moisture by capillary action. The fluid wicking capacity of a medium can be measured by grams of fluid drawn per gram of tampon weight over a fixed period of time.

As used herein "fluid wicking overwrap" refers to the liquid pervious material covering the exterior surface of the compressed absorbent member, substantially permeating the inner region of the compressed absorbent member, and extending below the withdrawal end to form a skirt portion. The fluid wicking overwrap may comprise a fibrous nonwoven material comprising a blend of synthetic and natural fibers. The synthetic fibers include but are not limited to fibers such as polyester, polyolefin, nylon, polypropylene, polyethylene, polyacrylic, cellulose acetate or bicomponent fibers. Natural fibers include but are not limited to those commonly known to be non-synthetic and of natural origin such as cotton and/or rayon. In general, the natural fibers provide ready absorption and fluid wicking strength. The synthetic fibers balance the capillary strength of the blended material, enabling the tampon to more readily slip against moist tissue, resulting in easier removal and hence removal comfort. The ratio of synthetic fibers to natural fibers may fall in the range of from about 90:10 to about 30:70. Alternatively, the ratio of synthetic fibers to natural fibers fall in the range of from about 70:30 to about 40:60.

The synthetic fibers may have hydrophobic and/or hydrophilic finishes. The synthetic fibers may be inherently hydrophilic, or may be treated to provide such properties. The overwrap may be formulated with some level of hydrophobic fibers as well, as long as it does not significantly diminish the fluid wicking strength of the overwrap of the tampon.

The blend of fibers forming the overwrap can be made by any number of techniques. The blends may be carded on webs. Commonly, carded webs that are hydroentangled, thermally bonded, and resin bonded all have application. In the latter case, the resin bonding agent can be used in place of the synthetic fibers as the method for tempering the aggressiveness of the natural fiber matrix. In this case, all natural fiber may be used with a significant portion of synthetic binder (10–30% is common). Spunbond and meltblown processes, combining synthetic fibers extruded/spun onto/into a mat or carded web of natural fibers provide other acceptable techniques. The basis weight of the fluid wicking overwrap may fall into a range from about 10 to about 60 grams per square meter, alternatively from about 15 to about 30 grams per square meter.

The fluid wicking overwrap may possess a horizontal wicking capacity of at least about 2, alternatively from about 3 to about 6 grams of fluid per gram of tampon at a 500 second interval. In one embodiment, the overwrap is 50% rayon, 50% polyester hydroentangled available as BBA 140027. Another embodiment includes a material that is dual layered with an outside and inside layer, made in accordance with U.S. Pat. No. 5,273,596. In this case, the outside layer is a 75% hydrophilic polypropylene with a 2.2 dpf and 25% 1.5 dpf rayon. The inside layer is 25% hydrophilic polypropylene with a 2.2 dpf and 75% 1.5 dpf rayon. The basis weights of the layers can vary, having from about 10 to about 15 grams per square meter in each layer. The resultant material is a 50% rayon 50% polypropylene thermally bonded blend with a basis weight from about 20 to about 30 grams per square meter. Both materials are produced by BBA Corporation of South Carolina, U.S.A.

As used herein "compressed" refers to pressing or squeezing together or otherwise manipulating the size, shape, and/or volume to obtain a tampon having vaginally insertable shape.

As used herein, "vaginally insertable shape" refers to the geometrical form of the absorbent tampon after compression. The tampon may be compressed into a generally cylindrical configuration in the radial direction along the longitudinal and/or lateral axes, axially, or in both the radial and axial directions. An example of a typical compressed tampon is one which is about 10–16 mm wide and about 40–50 mm long depending on absorbency. While the tampon may be compressed into a substantially cylindrical configuration, other shapes are possible. These may include shapes having a cross section that may be described as rectangular, triangular, trapezoidal, semi-circular, hourglass, or other suitable shapes.

Unless specifically stated otherwise, as used herein a first material is "substantially covering" or "substantially covers" a second material when the first material covers at least about 75%, typically at least about 90% of the surface area of the second material.

As used herein "adhesion to tissue" refers to the undesired union of the exterior surface of the tampon with the internal surface of the vagina, believed to be caused by both mechanical and capillary action. The capillary action refers to the tendency of the exterior surface of a tampon to attract or suction itself to the walls of the vaginal cavity until it is satisfied by fluid due to the capillary strength of the exterior surface. Mechanical action is related to the level of surface contact and the roughness of the substrate. Such adhesion is typically associated with an uncomfortable, or even painful, sensation when the tampon is inserted and/or withdrawn from the vaginal cavity due to tugging or pulling of the rugae (or folds) of the vaginal wall.

"Non-aggressive" materials as used herein refers to a materials low tendency to cause an adherence to tissue.

As used herein "substantially permeating" or "substantially permeates" refers to the manner in which the fluid wicking overwrap is positioned in relation to the inner region of the compressed absorbent member. As shown in the figures, the fluid wicking overwrap extends from the exterior surface and follows the spiral (in the case of rolled) or serpentine (in the case of the folded) contours of the compressed absorbent member and thereby extends into the inner region of said member along the interstices formed by the contours of said rolls or folds positioned in relation to the inner region of the compressed absorbent member. Any other compression method resulting in the fluid wicking overwrap similarly following the contours of the compressed absorbent member within the inner region are also acceptable.

The term "joined" or "attached" as used herein, encompasses configurations in which a first element is directly secured to second element by affixing the first element directly to the second element; configurations in which the first element is indirectly secured to the second element by affixing the first element to intermediate member(s) which in turn are affixed to the second element; and configurations in which first element is integral with second element; i.e., first element is essentially part of the second element.

The term "rolled" as used herein, is the configuration of the compressed absorbent member after winding the absorbent material substantially covered by the fluid wicking overwrap in a spiral round and round upon itself.

The term "folded" as used herein, is the configuration of the compressed absorbent member that may be incidental to lateral compaction of the absorbent material substantially covered by the overwrap or may purposely occur prior to a compression step. Such a configuration is readily recognizable, for example, when the absorbent material abruptly changes direction such that one part of the absorbent material bends and lies over another part of the absorbent material.

As used herein, "cm" is centimeter, "mm" is millimeters, "ml" is milliliters "g" is grams, "gsm" is grams per meter squared, "dpf" denier per foot, "sec" is seconds.

While particular embodiments of the present invention have been illustrated and described, it would be obvious to those skilled in the art that various other changes and modifications can be made without departing from the spirit and scope of the invention.

FIG. 1 shows one embodiment of such an absorbent tampon 20. The present invention, however, is not limited to a structure having the particular configuration shown in the drawings. The compressed absorbent member 22 (sometimes referred to as the "absorbent core") of the tampon 20 is shown in FIG. 1. The compressed absorbent member has an exterior surface 26. The compressed absorbent member has an inner region 24 shown in greater detail below. To form a tampon ready for use, the absorbent material and the fluid wicking overwrap 40 is typically compressed and optionally heat conditioned in any suitable conventional manner.

The exterior surface 26 of the compressed absorbent member 22 is substantially covered by the fluid wicking overwrap 40. This compressed primary absorbent also includes a skirt portion 44. The skirt portion 44 is comprised of fluid wicking overwrap 40 extending over the withdrawal end of the absorbent material 28 as show in greater detail below. In one embodiment, the tampon 20 includes a withdrawal means 48 as described below in more detail.

Figure 2:
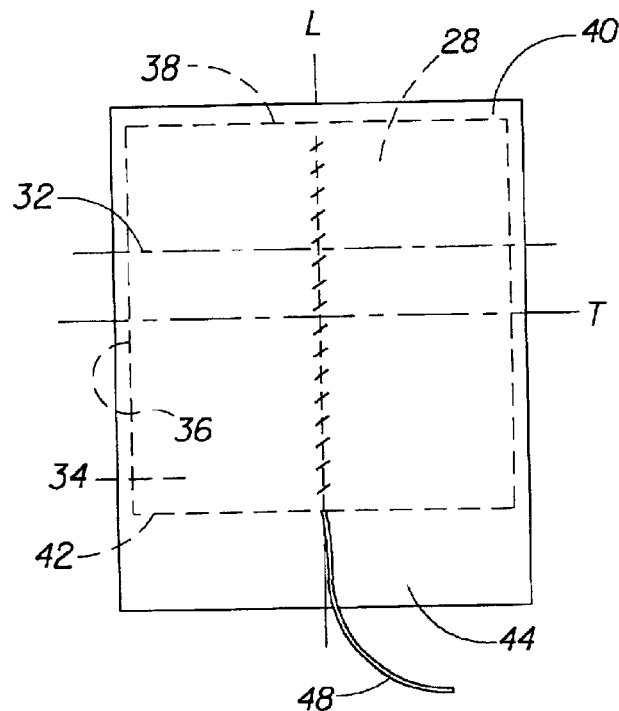
FIG. 2 is a plan view the assembled absorbent material and fluid wicking overwrap prior to compression.

FIG. 2 shows the fluid wicking overwrap 44 substantially covering the absorbent material 28 prior to compression. The absorbent material 28 has a first surface 34 opposed to the second surface 36 and an insertion end 38 opposed to a withdrawal end 42. The absorbent material has both a longitudinal axis and a transverse axis indicated by the lines marked "L" and "T" respectively.

The first surface 34 and opposed second surface 36 of the absorbent material 28 is substantially covered fluid wicking overwrap 40. The fluid wicking overwrap is positioned around the absorbent material so that the fluid wicking overwrap 40 may be proximate with the insertion end 38. The fluid wicking overwrap overlaps at the seam 32. The fluid wicking overwrap 40 may extend beyond the withdrawal end 42 to form a skirt portion 44. In one embodiment, the tampon 20 includes a withdrawal means 48.

Figure 3:
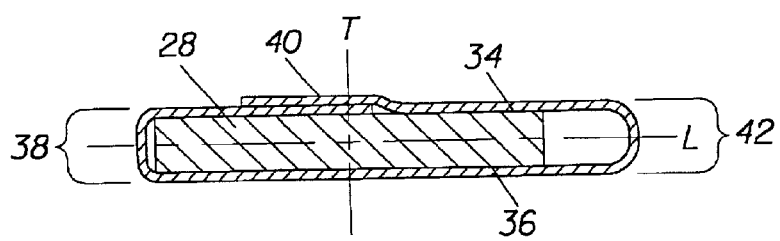
FIG. 3 is a longitudinal cross section of the absorbent material and fluid wicking overwrap prior to compression.

FIG. 3 shows a longitudinal cross section of the absorbent material 28 and fluid wicking overwrap 40 prior to compression. The absorbent material has a first surface 34 opposed to the second surface 36 and an insertion end 38 opposed to a withdrawal end 42. The absorbent material 28 is located in the center of the longitudinal cross-section. The fluid wicking overwrap 40 is positioned around the first surface 34 of the absorbent material 28 and opposed to the second surface 36.

Figure 4A:
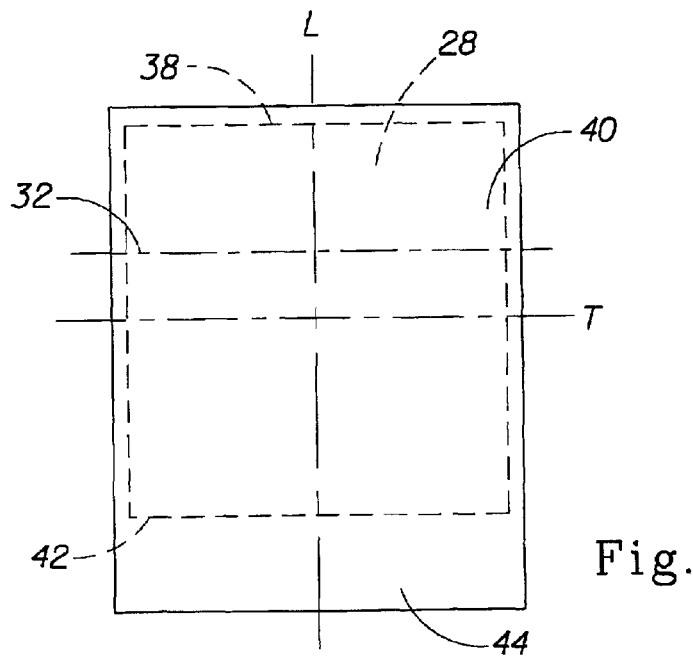
FIG. 4A is a plan view of the absorbent material with the fluid wicking overwrap wrapped longitudinally around the absorbent material.

FIG. 4A shows a pre-compression combination of absorbent material 28, fluid wicking overwrap 40. In the embodiment shown, the fluid wicking overwrap 40 is positioned around the first surface 34 and an opposed second surface (not shown) by wrapping around the longitudinal axis "L" of the absorbent material 28. The seam 32, where the fluid wicking overwrap 40 overlaps with itself, is shown above the transverse axis "T". The fluid wicking overwrap extends 40 beyond the withdrawal end 42 of the absorbent material 28 to form a skirt portion 44.

Figure 4B:
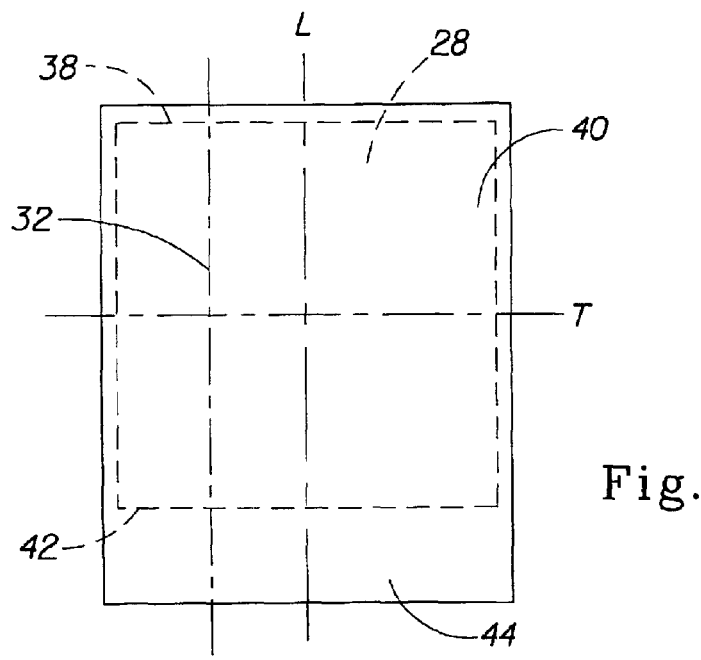
FIG. 4B is a plan view of the absorbent material with the fluid wicking overwrap wrapped transversely around the absorbent material.

FIG. 4B shows a pre-compression combination of absorbent material 28, fluid wicking overwrap 40. In the embodiment shown, the fluid wicking overwrap 40 is positioned around the first surface 34 and the second surface by wrapping around the transverse axis "T" of the absorbent material 28. The seam 32, where the fluid wicking overwrap 40 overlaps with itself, is shown to the left of the longitudinal axis "L". The fluid wicking overwrap 40 extends beyond the withdrawal end 42 of the absorbent material 28 to form a skirt portion.

Figure 5A:
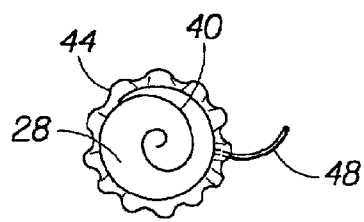
FIG. 5A is a cross sectional view of the compressed absorbent member that is of rolled construction from its insertion end.

FIG. 5A shows a cross-section of the compressed absorbent member. In the embodiment shown, the compressed absorbent member was constructed by substantially covering the absorbent material 28 with the fluid wicking overwrap 40 and forming a skirt portion 44. The absorbent material 28 and fluid wicking overwrap 40 are rolled prior to compression. The resulting cross section therefore has a spiral of fluid wicking overwrap 40 within the inner region of the compressed absorbent member. In the embodiment shown, the tampon has a withdrawal means 48.

Figure 5B:
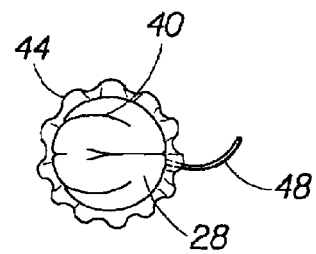
FIG. 5B is a cross sectional view of the compressed absorbent member that is of folded construction from its insertion end.

FIG. 5B shows a cross-section of the compressed absorbent member. In the embodiment shown, the compressed absorbent member was constructed by substantially covering the absorbent material 28 with the fluid wicking overwrap 40 and forming a skirt portion 44. The absorbent material 28 and fluid wicking overwrap 40 are folded. The resulting cross section therefore, has a serpentine pattern of fluid wicking overwrap 40 within the inner region of the compressed absorbent member. This serpentine pattern can take many shapes according to the folding process. In the embodiment shown, the tampon has a withdrawal means 48.

I. Tampon of the Present Invention

The tampon 20 of the present invention comprises a compressed absorbent member 22 comprising an absorbent material 28 and fluid wicking overwrap 44 that substantially covers the exterior surface 26 of the compressed absorbent member, substantially permeates the inner region 24 of the compressed absorbent member and extends beyond the withdrawal end to form a skirt portion.

a. Absorbent Material

The absorbent material 28 may be any suitable size and thickness suitable for compression into a tampon having a vaginally insertable shape. In the embodiment shown in FIG. 2, the absorbent material is generally square or rectangular, but other shapes such as trapezoidal, triangular, hemispherical, chevron and hourglass shaped are also acceptable. A typical size for absorbent material prior to compression may be from about 40 mm to about 100 mm in length and from about 40 mm to about 80 mm in width. In general, the absorbent material may be from about 40 mm to about 60 mm in length and from about 50 mm to about 70 mm in width. The typical range for the overall basis weight is from about 150 gsm to about 800 gsm.

The absorbent material may be a laminar structure comprised of integral or discrete layers. In other embodiments, the pad need not have a layered structure at all. The absorbent material may comprise a folded structure or may be rolled. The resulting compressed absorbent member 22 of the tampon 20 may be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials include creped cellulose wadding; melt-blown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Typical absorbent materials comprise cotton, rayon folded tissues, woven materials, non-woven webs, synthetic and/or natural fibers or sheeting. The tampon and any component thereof may comprise a single material or a combination of materials. Additionally, superabsorbent materials, such as super polymers or absorbent gelling and open-celled foams, materials may be incorporated into the tampon.

The materials for the tampon can be formed into a fabric, web, or batt that is suitable for use in the absorbent material by any suitable process such as airlaying, carding, wetlaying, hydroentangling, needling or other known techniques.

In another non-limiting embodiment, the absorbent material and resulting compressed absorbent member comprise rayon, cotton, or combinations of both materials. These materials have a proven record of suitability for use in the human body. The rayon used in the absorbent material may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), also available from Acordis Fibers Ltd. is also suitable. Any suitable cotton material may be used in the compressed absorbent member. Suitable cotton material includes, long fiber cotton, short fiber cotton, cotton linters, T-fiber cotton, card strips, and comber cotton. Preferably, the cotton layers should be scoured and bleached cotton absorbent with a glycerin finish, or other suitable finish.

If the compressed absorbent member of the present invention is layered, the layers may comprise different materials. For example, in one embodiment, the outer layers may comprise primarily rayon, while the intermediate layer or layers may comprise primarily cotton. Optionally, the entire compressed absorbent member may comprise a uniform or non-uniform blend of materials throughout. In one layered embodiment, each of the layers may comprise essentially 100% of the same material, such as outer layers of 100% rayon and an intermediate layer of 100% cotton. A Super Plus absorbency tampon of the present invention may be made from a pledget comprising about 100% rayon fibers. A Super absorbency or regular absorbency tampon of the present invention may be made from a pledget comprising about 25% cotton and about 75% rayon fibers. A Junior absorbency tampon may be made from a pledget comprising about 50% cotton and about 50% rayon fibers.

Pressures and temperatures suitable for compression are well known in the art. Typically, the absorbent material and the fluid wicking overwrap are compressed in the radial direction and optionally axially by any means well known in the art. While a variety of techniques are known and acceptable for these purposes, a modified tampon compressor machine available from Hauni Machines, Richmond, Va., is suitable.

b. Fluid Wicking Overwrap:

In the embodiments shown, the fluid wicking overwrap material 40 is generally rectangular, but other shapes such as trapezoidal, triangular, hemispherical, chevron, hourglass shaped, "T" and "L" shaped are also acceptable. Optimally, the fluid wicking overwrap may correspond to the shape of the absorbent material. The fluid wicking overwrap is positioned around the absorbent material so that the fluid wicking overwrap may be proximate with the insertion end of the absorbent material. In this regard, the fluid wicking overwrap could exactly match up to the insertion end or could for example extend from about 2 mm to about 8 mm over the insertion end. As well, the fluid wicking overwrap may extend beyond the withdrawal end to form a skirt portion as discussed below.

Because the fluid wicking overwrap can be wrapped in the various configurations, the width of the fluid wicking overwrap may vary. The width of the fluid wicking overwrap may be wider or less wide than the measure of the longitudinal or transverse axis of the absorbent material it is being wrapped around.

The fluid wicking overwrap substantially covers both the first surface and the second surface of the absorbent material. "Substantially covers" in this case means that the fluid wicking overwrap covers at least about 75%, optionally at least about 90% of the combined surface area of the first surface and the second surface. Thus, for example, the fluid wicking overwrap "substantially covers" the first surface and the second surface of the absorbent material when it covers 100% of the first surface and 50% of the second surface. The fluid wicking overwrap may be wrapped around the longitudinal axis "L" or the transverse axis "T" as shown in the attached figures in another embodiment. As well, two separate pieces of fluid wicking overwrap can sandwich the absorbent material.

The fluid wicking overwrap may be joined to the absorbent material by any variety of means. The fluid wicking overwrap may be joined to itself or to the absorbent material. For example, one portion of fluid wicking overwrap may be joined to an opposed portion of the fluid wicking overwrap or the absorbent member using any suitable adhesive or heat/pressure bonding means. Such adhesive may extend continuously along the length of attachment or it may be applied in a "dotted" fashion at discrete intervals. One method of heat bonding includes thermally bonding, fusion bonding, or any other suitable means known in the art for joining such materials. Alternatively, the fluid wicking overwrap may be joined to the absorbent material along with the withdrawal cord by stitching as shown in FIG. 2. Such stitching may use natural or synthetic thread.

The fluid wicking overwrap substantially permeates the inner region of the compressed absorbent member and allows the tampon to expand quickly providing good coverage against leakage. Not to be limited in theory, it is believed that substantial permeation of the fluid wicking overwrap allows for better or faster utilization of the absorbent material by wicking the fluid into all areas of the absorbent material.

c. Skirt Portion

The fluid wicking overwrap may extend beyond the withdrawal end to form a skirt portion 44. The length of the skirt portion is not critical. Typically, the fluid wicking overwrap can extend from about 2 mm to about 30 mm beyond the withdrawal end of the absorbent material. Typically, the fluid wicking overwrap extends from about 5 mm to about 20 mm beyond the withdrawal end of the absorbent material. In one embodiment, the skirt portion may not be compressed.

Both the compressed absorbent member and skirt portion of the fluid wicking overwrap may reside entirely within the vaginal cavity of the wearer during use of the tampon. This is achieved by the relative closeness of the skirt portion to the withdrawal end of the absorbent material as well of the relative size compared to the overall size of the tampon. In particular embodiments, only the withdrawal cord or other withdrawal means resides externally to the orifice of the vagina.

d. Optional Components

Optionally, the tampon of the present invention could include an additional overwrap that is non-aggressive. This additional overwrap would substantially cover the fluid wicking overwrap that substantially covers the exterior surface of the compressed absorbent member of the tampon. The additional overwrap need only extend as to be proximate with the withdrawal end of the absorbent material so that the entire skirt portion of the tampon is left uncovered by the additional overwrap. This additional overwrap could be added prior to or subsequent to compression.

In one embodiment, the tampon of the present invention may comprise a withdrawal means. The withdrawal means could be joined to the tampon and graspable for digital removal after use. The withdrawal means may be joined to at least the primary compressed absorbent member and extends beyond at least the withdrawal end. Any of the withdrawal means currently known in the art may be used as a suitable withdrawal mechanism. In addition, the withdrawal means can take on other forms such as a ribbon, loop, tab, or the like. The withdrawal means may be integral with the absorbent material.

The withdrawal means may be non-absorbent along at least the location of attachment to the absorbent material. As used herein, the term "non-absorbent" refers to a structure that does not retain a significant portion of deposited fluid in its structure. The entire withdrawal means may be made non-absorbent, if desired. The materials comprising the withdrawal means may be inherently non-wettable or hydrophobic, or they may be treated to provide such properties. For example, a coating of wax may be applied to the withdrawal cord to decrease or eliminate its absorbency. The withdrawal means need not necessarily be non-wicking, even if a non-absorbent withdrawal cord is desired.

The withdrawal means may be attached in any suitable manner known in the art including sewing, adhesive attachment, or a combination of known bonding methods. The withdrawal means may be joined to any suitable location on the tampon.

The tampon of the present invention may be inserted digitally or through the use of an applicator. Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable.

II. Process of Making

While several methods of making the tampon of the present invention should be apparent to one of skill in the art in light of the disclosure herein, following is a description of one method of making a tampon of the present invention.

The process for making a tampon comprises the steps of providing an absorbent material having a first surface opposed to the second surface and an insertion end opposed to a withdrawal end. A fluid wicking overwrap is also provided. A wrapped absorbent is created by substantially covering said first surface and second surface with the fluid wicking overwrap. The fluid wicking overwrap extends beyond the withdrawal end of the absorbent material to form a skirt portion. The process may include providing a withdrawal means that is attached to the absorbent material.

The wrapped absorbent with a skirt is rolled or folded and/or compressed to form a compressed absorbent member having a vaginally insertable shape. Upon compression the fluid wicking overwrap substantially covers the exterior surface of the compressed absorbent member and permeates into the interstices of the inner region of the compressed absorbent member.

III. Test Methods a. Horizontal Gravimetric Wicking Test

The "horizontal gravimetric wicking capacity" is a measure of a materials ability to absorb fluid by capillary action. The Horizontal Gravimetric Wicking Test measures the horizontal gravimetric wicking capacity. This is an absorbency test that measures the uptake of fluid by a tampon as a function of time. This test is run at a controlled temperature of 73° F.±4° F. and humidity of 50%±4%. Tampon samples should be conditioned at this temperature and humidity level for about 24 hours prior to running the test. In this method, the sample is held horizontally in a holder suspended from an electronic balance. The tampon is constrained under 0.25 psi by a conformable member under air pressure that keeps the pressure relatively constant over the entire sample. The pressure represents body pressure within the vaginal cavity around a tampon. A plastic supply tubing containing the test fluid, which is the Artificial Menstrual Fluid described below, is connected to a fluid reservoir at zero hydrostatic head relative to the test sample. A meniscus of fluid is brought in contact with a point of the sample's skirt. The sample's skirt remains in contact with the fluid and is allowed to wick for 500 seconds. The increase in weight of the sample is recorded every 10 seconds and is used as a measure of fluid up-take versus time. Three duplicate samples of each embodiment should be run and the average weight increase used as the horizontal gravimetric wicking capacity of that embodiment.

i. Preparation of Artificial Menstrual Fluid:

Step 1: Dilute 2.5 ml of reagent grade 85–95% lactic acid to 27.5 ml with distilled water. Label as 8% lactic acid.

Step 2: Mix 10.0 g of KOH with 90 ml distilled water until completely dissolved. Label as 10% potassium hydroxide solution.

Step 3: Add 8.5 g sodium chloride and 1.38 g hydrous monobasic sodium phosphate to a flask and dilute to 100 ml with distilled water. Mix until completely dissolved. Label as monobasic sodium phosphate solution.

Step 4: Add 8.5 g sodium chloride and 1.42 g anhydrous dibasic sodium phosphate to flask and dilute to 100 ml with distilled water. Mix until completely dissolved. Label as dibasic sodium phosphate solution.

Step 5: Add 450 ml of the dibasic sodium phosphate solution to a 100 ml beaker and add monobasic sodium phosphate solution until the pH is lowered to 7.2±0.1. Label as phosphate solution.

Step 6: Mix 460 ml pf phosphate solution and 7.5 ml of 10% potassium hydroxide solution in a 100 ml beaker. Heat solution to 50° C. and then add 31 g sterilized gastric mucin (American Laboratories, Inc. Omaha Nebr.). Continue heating for 2.5 hours to completely dissolve the gastric mucin. Allow the solution to cool to less than 40° C. and then add 2.0 ml of 8% lactic acid solution. Autoclave mixture at 121° C. for 15 minutes, then allow the mixture to cool to room temperature. Mucin mixture should be used within & days label as gastric mucin solution.

Step 7: Mix 500 ml of gastric mucin solution and 500 ml of fresh, sterile defibrinated sheep blood (Cleveland Scientific, American Biomedical, Bath, Ohio) in a beaker. The sheep blood should have a packed cell volume of greater than 38. The resulting artificial menstrual fluid should have a viscosity at 23° C. of between 7.15 and 8.64 centistokes. Label as artificial menstrual fluid. Store refrigerated and use within 7 days.

IV. Examples

Example 1

A folded compressed tampon of the present invention was prepared. The tampon comprises an absorbent material of 75% rayon and 25% cotton fiber with a basis weight of 750 gsm having dimensions of about 70 mm in width and about 48 mm in length. The tampon also comprises an overwrap of hydroentangled 50% rayon and 50% polyester fibers with a basis weight of 37 gsm having dimensions of about 168 mm in width and about 58 mm in length. The overwrap is wrapped around the absorbent material such that about 10 mm of the overwrap extends beyond the withdrawal end of the tampon. The absorbent material and overwrap are compressed axially and longitudinally then heated to form a tampon pledget of approximately 14 mm diameter and approximately 46 mm length.

The Horizontal Gravimetric Wicking Test was performed on resulting tampon pledget. The tampon pledget was positioned as described in the Test Methods so that the end edge of the extended overwrap or skirt portion of the tampon is available to the meniscus of Artificial Menstrual Fluid. The resulting horizontal wicking capacity for the sample at 500 sec and the fluid uptake was 3.47±0.10 g of Artificial Menstrual Fluid per gram of tampon.

Example 2

A rolled tampon of the present invention was made. The tampon comprises an absorbent material of 75% rayon and 25% cotton fiber with a basis weight of 500 gsm having dimensions of about 100 mm in width and about 48 mm in length. The tampon also comprises an overwrap of hydroentangled 50% rayon and 50% polyester fibers with a basis weight of 37 gsm having dimensions of about 100 mm in width and about 58 mm in length. The overwrap is wrapped around the absorbent material such that 10 mm of the overwrap extends beyond the withdrawal end of the tampon. The absorbent material and overwrap are rolled together so that the overwrap forms the outside of the tampon, then compressed axially and longitudinally and heated to form a tampon pledget of approximately 14 mm diameter and approximately 46 mm length.

The Horizontal Gravimetric Wicking Test was performed on resulting tampon pledget. The tampon pledget was positioned as described in Test Methods so that the end edge of the extended overwrap of the skirt portion of the tampon is in contact with the meniscus of Artificial Menstrual Fluid. The resulting horizontal wicking capacity for the sample at 500 sec and the fluid uptake was 3.98±0.25 grams of Artificial Menstrual Fluid per gram of tampon.

Comparative Example 3

A comparative tampon is made. The tampon comprises an absorbent material of 75% rayon and 25% cotton fiber with a basis weight of 750 gsm having dimensions of about 70 mm in width and about 48 mm in length. The tampon also comprises an overwrap of hydroentangled 50% rayon and 50% polyester fibers with a basis weight of 37 gsm having dimensions of about 168 mm in width and about 48 mm in length. The overwrap is wrapped around the absorbent material such that no material extends above or below the length of the absorbent material. An strip of 100% hydroentangled rayon with basis weight 278 gsm having dimensions of about 68 mm in length and about 8 mm in width is placed down the middle of the tampon pad such that 20 mm extends beyond the withdrawal end of the tampon. The strip is sewn to the tampon pad using thread. The tampon components are compressed axially and longitudinally then heated to form a tampon pledget of approximately 14 mm diameter and approximately 46 mm length with a 20 mm strip of wicking material extending beyond the pledget.

The Horizontal Gravimetric Wicking Test was performed on resulting tampon pledget. The tampon pledget was positioned as described above so that the end edge of the wicking strip is in contact with the meniscus of Artificial Menstrual Fluid. The resulting horizontal wicking capacity for the sample at 500 sec and the fluid uptake was 1.66–±0.10 grams of Artificial Menstrual Fluid per gram of tampon.

Comparative Example 4

A comparative tampon is made similar in design to that disclosed in U.S. Pat. No. 6,248,075 B1 issued on Jul. 10, 2001 to The Procter & Gamble Company. The tampon comprises an absorbent material of 75% rayon and 25% cotton fiber with a basis weight of 780 gsm having dimensions of about 70 mm in width and about 48 mm in length. The tampons also comprises an overwrap of bicomponent polyethylene/polypropylene fibers made by Sandler with a basis weight of 17 gsm having dimensions of about 168 mm in width and about 48 mm in length. The overwrap is wrapped around the absorbent material such that no material extends above or below the length of the absorbent material. A cotton cord intermittently containing rayon sliver is sewn onto the middle of the tampon pad formed by absorbent material and overwrap, such that the portion of the cord containing rayon sliver extends approximately 15 mm into and approximately 25 mm beyond the withdrawal end of the tampon. The tampon components are compressed axially and longitudinally then heated to form a tampon pledget of approximately 14 mm diameter and approximately 46 mm length with a 25 mm length of wicking material extending below the pledget.

A tampon of The Horizontal Gravimetric Wicking Test was performed on resulting tampon pledget. The tampon pledget was positioned as described in Test Methods above so that the end edge of the wicking cord is in contact with the meniscus of Artificial Menstrual Fluid. The resulting horizontal wicking capacity for the sample at 500 sec the fluid uptake was 0.89±0.05 grams of Artificial Menstrual Fluid per gram of tampon.

What is claimed is:

1. A catamenial tampon comprising:
   a compressed absorbent member having an inner region and an exterior surface, said compressed absorbent member comprising an absorbent material;
   said absorbent material having a first surface opposed to a second surface and an insertion end opposed to a withdrawal end;

a fluid wicking overwrap substantially covering said first surface and said second surface of said absorbent material;

said fluid wicking overwrap extending beyond the withdrawal end of said absorbent material to form a fluid wicking skirt portion;

said fluid wicking overwrap substantially covering said exterior surface of the compressed absorbent member; and a portion of said fluid wicking overwrap substantially permeating said inner region of said compressed absorbent member.

2. A tampon according to claim 1 wherein the fluid wicking overwrap comprises synthetic fibers and natural fibers.

3. A tampon according to claim 2 wherein the ratio of synthetic fibers to natural fibers is from about 90:10 to about 30:70.

4. A tampon according to claim 1 wherein the fluid wicking overwrap has a horizontal gravimetric wicking capacity with a range of from about 2 to about 6 grams of fluid per gram of tampon at a 500 second interval.

5. A tampon according to claim 1 wherein said fluid wicking overwrap is hydroentangled and comprises about 50% rayon and about 50% polyester.

6. A catamenial tampon comprising:

a compressed absorbent member having an inner region and an exterior surface, said compressed absorbent member comprising an absorbent material;

said absorbent material having a first surface opposed to a second surface and an insertion end opposed to a withdrawal end;

a fluid wicking overwrap substantially covering said first surface and said second surface of said absorbent material;

said fluid wicking overwrap extending beyond the withdrawal end of said absorbent material to form a fluid wicking skirt portion;

said fluid wicking overwrap substantially covering said exterior surface of the compressed absorbent member;

a portion of said fluid wicking overwrap substantially permeating said inner region of said compressed absorbent member; and a withdrawal means for removal of said tampon attached to said compressed absorbent member and extending beyond at least said withdrawal end.

7. A tampon according to claim 6 wherein the fluid wicking overwrap is 100% rayon.

8. A tampon according to claim 6 wherein the fluid wicking overwrap has a horizontal gravinietric wicking capacity with a range from about 2.5 to about 5 grams of fluid per gram of tampon at a 500 second interval.

9. A tampon according to claim 6 wherein said fluid wicking overwrap comprises a 50% rayon 50% polypropylene thermally bonded blend.

10. A tampon according to claim 6 wherein said skirt portion extends from 2 mm to 20 mm from said withdrawal end of said absobent material.

11. A tampon according to claim 10 wherein the fluid wicking overwrap comprises synthetic fibers and natural fibers.

* * * * *